United States Patent [19]

Hirsch et al.

[11] 4,172,076
[45] Oct. 23, 1979

[54] PROCESS FOR PREPARING STEROIDAL ACIDS AND THEIR INTERMEDIATE DERIVATIVES

[75] Inventors: Arnold L. Hirsch, Oak Park, Ill.; Josef Pikl, Glassboro, N.J.

[73] Assignee: Diamond Shamrock Corporation, Cleveland, Ohio

[21] Appl. No.: 877,569

[22] Filed: Feb. 13, 1978

Related U.S. Application Data

[63] Continuation-in-part of Ser. No. 784,028, Apr. 4, 1977, abandoned.

[51] Int. Cl.² .................. C07J 17/00; C07J 9/00
[52] U.S. Cl. .................. 260/239.55 R; 260/397.1; 260/397.2; 260/397.4
[58] Field of Search .................. 260/239.55 R, 397.1; /Machine Searched Steroids

[56] References Cited

U.S. PATENT DOCUMENTS

| | | | |
|---|---|---|---|
| 3,786,062 | 1/1974 | Schroeder et al. | 260/397.2 |
| 3,801,607 | 4/1974 | Goffinet | 260/397.2 |

OTHER PUBLICATIONS

Organic Reactions III: 83–107 (1946), (John Wiley & Sons, Inc.), pp. 100, 101 and 105.

*Primary Examiner*—Ethel G. Love
*Attorney, Agent, or Firm*—Neal T. Levin; Leslie G. Nunn

[57] ABSTRACT

Steroidal acids of the formula

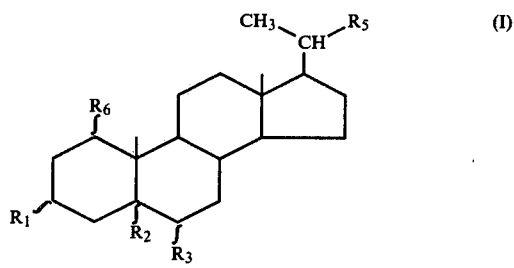

are prepared from steroidal ketones of the formula

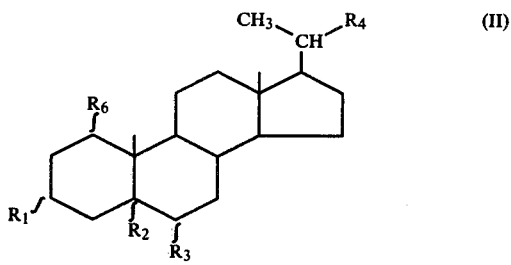

wherein $R_1$ is hydrogen; hydroxy; lower alkyloxy; tetrahydropyranyloxy; aryloxy; alkyl; alkanoyloxy or aroyloxy; $R_2$ is hydrogen; hydroxy; lower alkyloxy; tetrahydropyranyloxy; aryloxy; alkyl; alkanoyloxy or aroyloxy; $R_3$ is hydrogen; hydroxy; lower alkyloxy; tetrahydropyranyloxy; aryloxy; alkyl; alkanoyloxy or aroyloxy; with the proviso that $R_1$ and $R_2$ together or $R_2$ and $R_3$ together may form a carbon-carbon bond; $R_4$ is $-(CH_2)_nCO(CH_2)_mCH_3$; $R_5$ is $-(CH_2)_{n+m+1}COOH$; $R_6$ is hydrogen; hydroxy; lower alkyloxy; tetrahydropyranyloxy; aryloxy; alkyl; alkanoyloxy or aroyloxy; and n is 0 to 4, m is 0 to 4 and sum of $n+m$ is 0 to 4 in the formula (I) and (II) above and these formulas include isomers and homologs of the above mentioned compounds: by reacting 1 m of ketone with 1 to 70 m sulfur and 1 to 80 m of ammonia, primary amine or secondary amine to produce a thioamide which is then hydrolyzed to an acid. These acids are useful as intermediates in the synthesis of Vitamin D derivatives.

18 Claims, No Drawings

PROCESS FOR PREPARING STEROIDAL ACIDS AND THEIR INTERMEDIATE DERIVATIVES

CROSS-REFERENCES TO RELATED APPLICATIONS

This application is a continuation-in-part of U.S. Ser. No. 784,028—Hirsch and Pikl, filed on Apr. 4, 1977, now abandoned.

BACKGROUND OF THE INVENTION

1. Field of the Invention

This invention relates to preparation of steroidal acids from steroidal ketones.

2. Description of the Prior Art

Commercial production of 25-hydroxy-Vitamin D3 requires a competitively priced intermediate. Readily available intermediates are limited. It is desirable that the steroidal nucleus be intact in the intermediate to avoid the difficult stereochemical problems associated with synthetically constructing the steroid molecule.

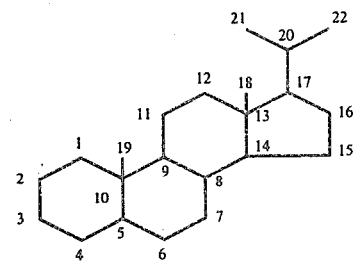

Of the available steroidal intermediates, 3 beta-hydroxycholenic acid, which was once available as the principal product of the oxidation of cholesterol and more recently from bile acid sources, is a convenient raw material because its side chain only needs to be extended by one carbon atom to obtain 3 beta-hydroxy-homocholenic acid and thence the esterified product may be treated with Grignard reagent (methyl magnesium bromide) to obtain 25-hydroxy-cholesterol, which may then be converted to the 7-dehydro-derivative and irradiated to obtain 25-hydroxy-Vitamin D3. When desired, the 7-dehydro-group may be introduced prior to treatment with Grignard reagent. A convenient laboratory synthesis of the 25-hydroxy cholesterol following this scheme may be found in R. I. Kau, A. Markus and Z. Goldschmitt, J. Chem. Soc., Perkin I, 2423 (1972). DeLuca's U.S. Pat. No. 3,772,361 also describes the conversion of 25-hydroxycholesterol to 25-hydroxy-7-dehydrocholesterol and claims cholest-5,7-dien-3 beta, 25-diol. Another useful raw material is hyodesoxycholic acid (3 alpha, 6 alpha-dihydroxy cholanic acid). U.S. Pat. No. 2,781,364—Ziegler et al, issued Feb. 12, 1957 teaches conversion of 3 alpha, 6 alpha-dihydroxy steroids to compounds with 3 beta-hydroxy delta$^5$ grouping.

Use of diazomethane to extend the side chain in the 3 beta-acetoxycholenyl chloride is a dangerous process on a large scale. Diazomethane is extremely explosive and is also chronically as well as acutely toxic. Handling of this diazomethane reaction requires many precautions which makes its large scale use uneconomical. There is a definite need for alternatives to the diazomethane method of lengthening the side chain of 3 beta-hydroxycholenic acid. Other reported processes for preparing 25-hydroxycholesterol or its intermediates are expensive, and/or low yielding. There is a need to produce 25-hydroxycholesterol precursors by economical methods.

The Willgerodt reaction was first described in 1887. It was used for the conversion of carbonyl compounds into acid amides using aqueous ammonium polysulfide. In 1923, the Kindler modification of the Willgerodt reaction was described in which the carbonyl compound is reacted with sulfur and a primary or secondary amine and generates a thioamide. This reaction involves migration of a carbonyl group along an aliphatic chain and is usually terminated by an oxidation step at the terminal carbon atom, forming an acid derivative. The amide products are characterized as having the same number of carbon atoms as the starting carbonyl compounds. The reaction has been extensively used to lengthen an aliphatic carboxylic acid chain by one carbon atom by converting the carboxylic acid to the corresponding methyl ketone, then treating the ketone under the Willgerodt-Kindler condition, and hydrolyzing the resulting thioamide to the homologous aliphatic carboxylic acid. The Willgerodt reaction has been used principally with aromatic compounds having aliphatic side chain because aliphatic ketones have not given good yields.

STATEMENT OF THE INVENTION

A process of preparing steroidal acids of the formula

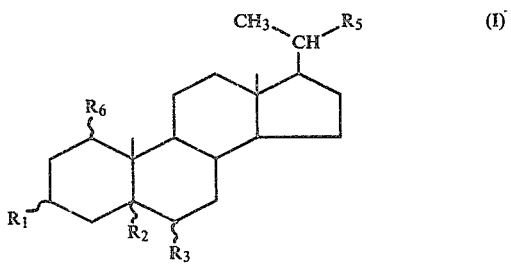

from steroidal ketones of the formula

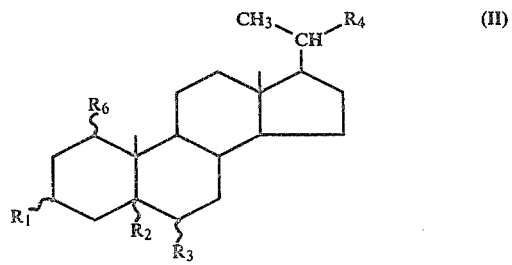

wherein:
$R_1$ is hydrogen; hydroxy; lower alkyloxy; tetrahydropyranyloxy; aryloxy; alkyl; alkanoyloxy or aroyloxy;

$R_2$ is hydrogen; hydroxy; lower alkyloxy; tetrahydropyranyloxy; aryloxy; alkyl; alkanoyloxy or aroyloxy;

$R_3$ is hydrogen; hydroxy; lower alkyloxy; tetrahydropyranyloxy; aryloxy; alkyl; alkanoyloxy or aroyloxy; with the proviso that $R_1$ and $R_2$ together or $R_2$ and $R_3$ together may form a carbon-carbon bond;

$R_4$ is $-(CH_2)_nCO(CH_2)_mCH_3$;

$R_5$ is $-(CH_2)_{n+m+1}COOH$;

$R_6$ is hydrogen, hydroxy; lower alkyloxy; tetrahydropyranyloxy; aryloxy; alkyl; alkanoyloxy or aroyloxy; and n is 0 to 4, m is 0 to 4 and sum of n+m is 0 to 4 in formulas (I) and (II) above and these formulas include isomers and homologs of the above mentioned compounds:

by reacting 1 m of ketone (II) with from about 1 m to about 70 m of sulfur and about 1 m to about 80 m of a base selected from the group consisting of ammonia, primary amines and secondary amines to obtain a thioamide and thereafter hydrolyzing the thioamide to obtain the acid. These acids are useful as intermediates in the synthesis of Vitamin D derivatives.

DESCRIPTION OF THE PREFERRED EMBODIMENTS

Reaction between the ketone, sulfur and base may be carried out at from about 125° C. to about 180° C. If desired, the reaction may be carried out under pressure or at atmospheric pressure. The thioamide may be hydrolyzed by refluxing in alcoholic potassium hydroxide or sodium hydroxide and acidifying with an acid such as hydrochloric acid to obtain the desired steroidal acid. Likewise, the thioamide may be hydrolyzed with an acid such as sulfuric acid at a temperature of from about 90° C. to about 150° C.

The following terms are used herein to characterize the steroidal ketones used in the reaction and steroidal acids produced in the reaction.

As used herein, the term "alkyl group" refers to a monovalent substituent having from 1 to 20 carbon atoms which may be straight or branched-chain. Examples of alkyl groups include methyl, ethyl, n-propyl, i-propyl, butyl, n-hexyl, octyl, decyl, dodecyl, octadecyl and the like.

The term "alkylene group" refers to a divalent substituent having from 1 to 20 carbon atoms which may be straight or branched-chain and whose free valences are attached to two distinct groups. Examples of alkylene groups are methylene, ethylene, propylene, butylene and the like as well as their isomers such as isopropylene, isobutylene and the like.

The term "alkoxy group" refers to a monovalent substituent of an alkyl group linked through an ether oxygen having its free valence bond from the ether oxygen. Examples of alkoxy groups are methoxy, ethoxy, isopropoxy, tert-butoxy, and the like, including a tetrahydropyranyloxy group.

The term "tertiary alkoxy group" refers to an alkoxy group in which the ether oxygen is linked to a carbon having 3 carbon substituents. Examples of tertiary alkoxy groups are butoxy, amyloxy and the like.

The term "phenyl alkoxy group" refers to an alkoxy group which is substituted by a phenyl ring. Examples of phenyl alkoxy groups are benzyloxy, 2-phenylethoxy, 4-phenylbutoxy and the like.

The term "alkanoyloxy group" refers to the residue of an alkylcarboxylic acid formed by removal of the hydrogen from the hydroxyl portion of the carboxyl group. Examples of alkanoyloxy groups are formyloxy, acetoxy, butyryloxy, hexanoyloxy and the like.

The term "substituted", as applied to "phenyl," refers to phenyl substituted with one or more of the following groups: alkyl, halogen such as fluorine, chlorine, bromine or iodine, nitro, cyano, trifluoromethyl and the like. The term "lower," applied to any of the aforementioned groups, refers to those groups having from 1 to 8 carbon atoms.

In the formulas, various substituents are illustrated as joined to the steroid nucleus by one of three notations: a solid line (—) indicating a substituent which is in the beta-orientation (i.e., above the plane of the molecule); a dotted line (---) indicating a substituent which is in the alpha-orientation (i.e., below the plane of the molecule), or a wavy line (~) indicating a substituent which may be in the alpha- or beta-orientation.

The term "base" includes nitrogen containing compounds such as ammonia, primary amines and secondary amines. Useful primary amines include monoalkylamines such as monomethylamine, monoethylamine, monopropylamine, monobutylamine and the like. Useful secondary amines include dialkylamines such as dimethylamine, diethylamine, dipropylamine, dibutylamine and the like, and cyclic amines such as morpholine, substituted morpholine and the like. It is to be understood these amines also include isomers and homologs of the above mentioned amines.

This process may be used to react a steroidal ketone such as homochol-5-en-3 beta-ol-24-one or one of its esters derived from an alcohol having from 2 to 8 carbon atoms to obtain 3 beta-hydroxy-25-homo-5-cholenic acid. Likewise, this process may be used to react a ketone such as homocholan-3 alpha, 6 alpha-diol-24-one or one of its esters derived from an alcohol having from 2 to 8 carbon atoms to obtain 3 alpha, 6 alpha-dihydroxy-25-homocholanic acid. This process may also be used to react a steroidal ketone such as norchol-5-en-3 beta-ol-22-one or one of its esters derived from an alcohol having from 2 to 8 carbon atoms to obtain 3 beta-hydroxy-24-nor-5-cholenic acid. Further, the process may be used to react a steroidal ketone such as homochol-5-en-3 beta-ol-22-one or one of its esters derived from an alcohol having from 2 to 8 carbon atoms to obtain 3 beta-hydroxy-25-homo-5-cholenic acid. Thus, this process permits conversion of available raw materials into useful intermediates for preparation of metabolites of Vitamin D. Table I below illustrates schematically use of this process in the preparation of these metabolites.

Additional details on the Willgerodt reaction and the Kindler variations may be found in Volume III of Organic Reactions (John Wiley & Sons, Inc. 1946) at pages 83-107. The teachings in this publication regarding reaction conditions, reagents such as ammonium polysulfide, amines, sulfur, hydrogen sulfide, solvents and other parameters as they apply to this invention are incorporated herein by reference.

For a fuller understanding of the nature and objects of this invention, reference may be made to the following examples which are given merely to illustrate the invention and are not to be construed in a limiting sense. All weights, proportions and percentages are by weight unless otherwise indicated. Likewise, all temperatures are °C. unless otherwise indicated.

TABLE I
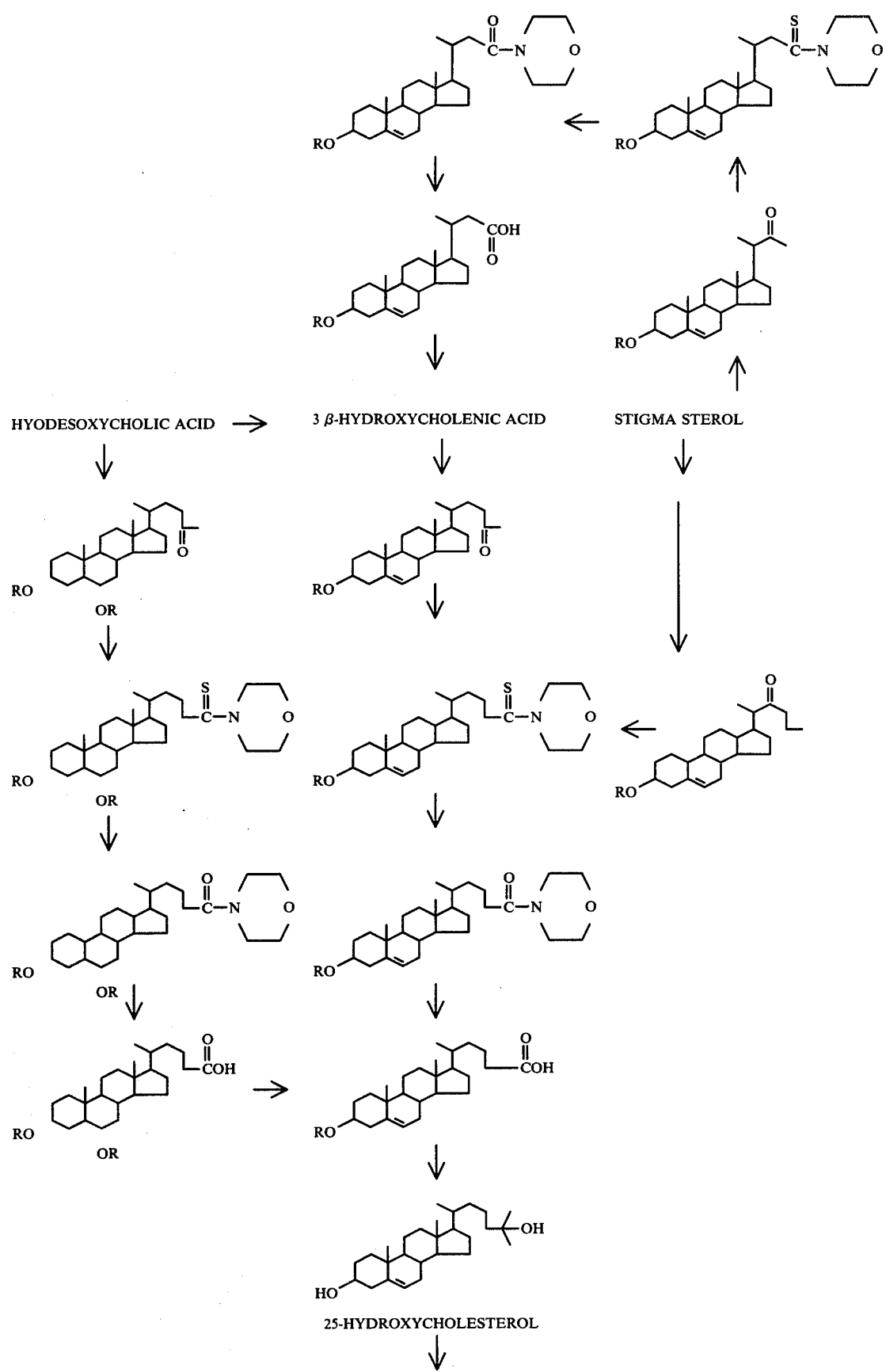
HYODESOXYCHOLIC ACID → 3 β-HYDROXYCHOLENIC ACID   STIGMA STEROL
25-HYDROXYCHOLESTEROL TABLE I-continued

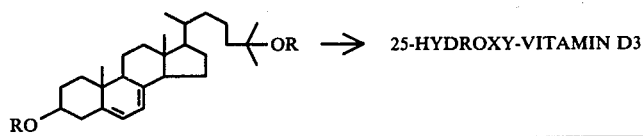

Where R is hydrogen, acyl, aryl or alkyl

EXAMPLE I

This example demonstrates preparation of 3 beta-hydroxy-25-homo-5-cholenic acid.

(A) Preparation of 3 beta-acetoxy-5-cholenic acid

A total of 112 g (0.3 m) of 3 beta-hydroxy-5-cholenic acid was added to a 3 l flask containing 560 g (9.3 m) glacial acetic acid and 574 g (5.6 m) acetic anhydride. The resulting reaction mixture was heated with agitation at 90°–95° C. for 3 hr. After heating, the reaction mixture was cooled to about 70° C. and 102 g water added over about 1 hr. Reaction with water was strongly exothermic. There was an induction period of up to 10 minutes before any heat of reaction was noticed. However, the reaction temperature went as high as 92° C. After water was added, the reaction mixture was maintained at 80°–85° C. for 0.5 hr and then preparations were made for vacuum distillation.

Under partial vacuum, 900 ml acetic acid were distilled from the reaction mixture by regulating the vacuum so as to maintain the temperature of the mixture at 70° C.±3° C. When the temperature fell to 65° C. or lower, it was necessary to reheat the mixture to about 80° C. to continue distillation. After the required amount of acetic acid was distilled off, vacuum was released. The reaction mixture was then refluxed and 66 ml methylene dichloride was added slowly to the refluxing mixture. Then the reaction mixture was cooled slightly and maintained at about 50° C. for 6 hr to obtain crystalline 3 beta-acetoxy-5-cholenic acid. The crystalline acid was filtered and the resulting filter cake washed 6 times using 100 ml hexane for each wash and then dried in a warm air drying cabinet. A yield of 104 g of product, which is equivalent to 84% theory, was obtained. The vacuum melting point of the acid was 190°/193°–95° C. and the melt was colorless. The filtrate and washes from the first crop of crystals were concentrated under vacuum to obtain 60 ml of a clear solution which was diluted with 60 ml hexane and the solution was allowed to crystallize by standing one day at room temperature. The second crop of crystals weighed 8.5 g which was equivalent to 6.8% theory and had a vacuum melting point of 191°–193° C. The two crops of crystals represented a yield of 90.8% of 3 beta-acetoxy-5-cholenic acid.

(B) Preparation of 3 beta-acetoxy-5-cholenic acid chloride

A total of 150 ml purified thionyl chloride was charged under anhydrous conditions into a 250 ml 3-neck flask equipped with mechanical agitator and cooled to −15° C. Then 50.0 g (0.12 m) 3 beta-acetoxy-5-cholenic acid from Section (A) above was added to the cooled thionyl chloride over a few minutes to obtain a viscous reaction mixture which was then maintained at −15°±2° C. for 3 hr. After 1.5 hr at −15° C., the solid present in the reaction mixture completely dissolved.

The reaction temperature was allowed to rise to 15° C. over 1 hr, then over 0.5 hr to 30° C. and maintained at 30° C. for 0.5 hr. Vacuum was then applied and distillate from the reaction mixture was collected in a receiver immersed in a freezing mixture. The flask containing the reaction mixture was then placed in a water bath and the bath temperature was gradually raised from 30° C. to 60° C. After most of the thionyl chloride distilled off, the reaction product in the flask solidified. The water bath temperature was then maintained at 55°–60° C. for 2 hr to remove the last traces of thionyl chloride.

Weight of the reaction product, the acid chloride, was almost theoretical (52.1 g). The product 3 beta-acetoxy-5-cholenic acid chloride, was a grayish color solid melting at 157°–159° C. which can be used in most of the preparations "as is" without purification and stored in a dessicator over potassium hydroxide pellets until used.

Thionyl chloride recovered from this reaction was very pure and was reused without further purification. Recovery of thionyl chloride can be improved by more efficient cooling of the receiver.

(C) Preparation of 25-homochol-5-en-3 beta-ol-24-one 3-acetate

A 100 ml aliquot of 2.94 molar Grignard reagent (methyl magnesium bromide) was diluted with 300 ml of dry diethyl ether and 42 g of dry cadmium bromide was added at 15°–20° C. over 20 min. Initially, the cadmium bromide dissolved in the ether, but near the end of the addition, a second very mobile liquid phase formed under the ether layer. Volume of the bottom layer was about one-third of the volume of the top layer. After all of the cadmium bromide was added, the reaction mixture was agitated for 1 hr at 20° C.±1° C. At this point, there was no noticeable change in the viscosity of the bottom layer.

A solution of 54 g of 3 beta-acetoxy-5-cholenic acid chloride from (B) above dissolved in 200 ml of dry benzene, was added to the dimethyl cadmium reaction mixture over 20 min at 20° C. Slight cooling was necessary, particularly during the initial phase of the acid chloride addition. As reaction progressed, the bottom layer became more viscous, but solid did not form at any time during the addition. After 30 min, reaction was essentially complete but the reaction mixture was maintained for a total of 2.5 hr at 20°±1° C. before being processed in the following manner.

First, the reaction mixture was cooled to about 15° C. and 100 g crushed ice was added very slowly, particularly at the start of the addition. The initial ice addition was slightly exothermic and thickened the reaction mixture for a short time. Temperature rose to about 30° C. After all of the ice was added, the reaction mixture became quite fluid again. Then the mixture was acidified by slowly adding 30 ml of 1:1 mixture of 37% hydrochloric acid and water. Two clear layers were formed. The aqueous bottom layer was drawn off and discarded while the top layer was washed once with 200 ml water, separated, filtered and evaporated on a steam bath under vacuum. The product, 25-homochol-5-en-3 beta-ol-24-one 3-acetate, was then recrystallized from a concentrated benzene solution to obtain a light tan-colored solid which after drying yielded 51.0 g of crude product having a melting point of 148°–151° C.

(D) Preparation of 25-homochol-5-en-3 beta-ol-24-one

A 1.0 g sample of 25-homochol-5-en-3 beta-ol-24-one 3-acetate was dissolved in a solution containing 2 g potassium hydroxide in 40 ml of methanol and the mixture reacted by refluxing for 15 min. The reaction mixture was then poured into 200 ml of water containing 6 ml of concentrated hydrochloric acid to precipitate the product which was filtered after 30 min agitation at room temperature, washed free of acid with water and dried.

The dry product was recrystallized from 10 ml methanol, in which it was readily soluble hot, by crystallization on cooling to room temperature. The slurry of crystals was cooled to 10° C., filtered and washed with cold methanol to obtain a yield of 0.73 g. A t.l.c. (thin layer chromatography on silica gel, developed with a mixture of 91% dichloroethane and 9% methanol, showed only a trace of an impurity, which was much more polar than main spot. Melting point of the product after drying in vacuo at 95° C. was over a wide range, 125°–135° C. The product, 25-homochol-5-en-3 beta-ol-24-one, on crystallization from 60 parts by weight of a 1:1 mixture of benzene and hexane had a vacuum melting point of 130°–135° C. A sample was dried in vacuo at 56° C. for 10 hours and analyzed for C and H to obtain the following results:

| Found | Calc. for $C_{25}H_{40}O_2$ |
|---|---|
| %C: 80.22 | 80.6 |
| %H: 10.79 | 10.8 |

(E) Reaction of 25-homochol-5-en-3 beta-ol-24-one 3-acetate with morpholine and sulfur A total of 3.5 g of 25-homochol-5-en-3 beta-ol-24-one 3-acetate obtained in (C) above, was slowly added to 1.25 ml morpholine which had been heated to 80°–100° C. After heating a few minutes at 100° C., a clear solution was obtained. Then 0.45 g sulfur was added and the reaction mixture heated at 125°–130° C. for 2 hr. Shortly after sulfur addition, evolution of hydrogen sulfide was noticed. Gas evolution gradually decreased. After heating for 2 hr, the reaction mixture was diluted with 5 ml morpholine and the diluted mixture poured into 100 ml water with agitation. After 0.5 hr of agitation, the reaction mixture was acidified with dilute hydrochloric acid, agitated for an additional hr, filtered and washed with cold water. The precipitate was dried to obtain 4.1 g of crude thioamide, 3 beta-acetoxy-25-homo-5-cholenic acid thiomorpholide. The ratio of steroid: sulfur: amine was 1:1.7:1.7.

The crude thioamide was partially purified by dissolving in a small amount of tetrahydrofuran and then adding hexane. The crystals which formed on standing were collected, filtered and washed with hexane.

Analysis of the crystals gave the following results:

| Found | Calc. for $C_{31}H_{49}O_2NS$ |
|---|---|
| %C: 72.39 | 72.23 |
| %H: 9.62 | 9.51 |
| %N: 2.47 | 2.72 |
| %S: 6.45 | 6.21 |

(F) Preparation of 3 beta-hydroxy-25-homo-5-cholen-morpholide

The crude thioamide obtained in (E) above was hydrolyzed under mild conditions, i.e., by refluxing in 10 parts of 10% methanolic potassium hydroxide diluted with an equal volume of benzene. Reflux temperature of this mixture was 58° C.

An acidic fraction which was extracted with dilute alkali and a neutral fraction, which was not soluble in dilute alkali were isolated from the reaction mixture. The acidic fraction was identified as 3 beta-hydroxy-25-homo-5-cholenic acid with a melting point of 214°–216° C., gave no depression in melting point when mixed with an authentic sample of 3 beta-hydroxy-25-homo-5-cholenic acid prepared from 3 beta-hydroxy-5cholenic acid by the diazomethane route.

The neutral fraction sample after crystallization from ethyl acetate had a melting point of 182°–183.5° C. Elemental analysis gave the following results:

| Found | Calc. for $C_{29}H_{47}O_3N$ |
|---|---|
| %C: 76.16 | 76.08 |
| %H: 10.41 | 10.35 |
| %N: 2.88 | 3.06 |
| %S: 0.2 | Nil |

The results agree very well with those for 3 beta-hydroxy-25-homo-5-cholenmorpholide.

(G) Preparation of 3 beta-hydroxy-25-homo-5-cholenic acid

A 2.0 g (0.00389 m) sample of crude thioamide from (E) above was added to a solution of 4 g potassium hydroxide dissolved in 13 ml ethanol and 0.5 ml water. The resulting mixture was refluxed for 5 hr at 89°–90° C. to hydrolyze the crude thioamide. Hydrolysis was followed using thin layer chromatography. During hydrolysis, the spot which corresponded to the thioamide gradually became weaker until at the end of hydrolysis, there was essentially the one product, 3 beta-hydroxy-25-homo-5-cholenic acid. After hydrolysis, mixture was diluted with 10 ml ethanol to obtain an alcoholic solution which was heated until the small amount of solid that had separated dissolved. The alcoholic solution was then poured into 200 ml water containing 10 ml concentrated hydrochloric acid and formed a fluffy precipitate. This precipitate was filtered, washed with water and dried to obtain a light tan colored product, 3 beta-hydroxy-25-homo-5-cholenic acid, weighing 1.55 g and representing the theoretical yield. Recrystallization of 1.0 g of this crude product from a mixture of dichloroethane and methanol gave 0.55 g of first crop crystals. The melting point of these crystals was 210°/212°–214° C. which was identical with the melting point of an authentic sample prepared from 3 beta-hydroxy-5-cholenic acid by the diazomethane route.

EXAMPLE II

This example demonstrates preparation of 3 beta-hydroxy-25-homo-5-cholenic acid from 25-homo-5-cholen-3 beta-ol-24-one 3-acetate.

A 8.51 g sample of 25-homo-5-cholen-3 beta-ol-24-one 3-acetate was reacted with 0.8 g of sulfur and 3 g of morpholine for 1 hr at 130° C. and 2 hr at 138°-140° C., then the crude reaction product was isolated by pouring the reaction mixture into water and filtering. Yield of the crude reaction mixture was 9.3 g. On hydrolysis with caustic potash in ethyl alcohol, an 85% (by weight) yield of crude 3 beta-hydroxy-25-homo-5-cholenic acid was obtained. Assay by thin layer chromatography indicated that the acid was approximately 70% pure 3 beta-hydroxy-25-homo-5-cholenic acid. The ratio of steroid: sulfur: amine was 1:1.2:1.7.

EXAMPLE III

This example demonstrates preparation of 3 beta-hydroxy-25-homo-5-cholenic acid from 25-homochol-5-en-3 beta-ol-24-one 3-acetate.

A 8.51 g sample of 25-homochol-5-en-3beta-ol-24one 3-acetate was added to 4.3 g morpholine at 120° C. and then 0.8 g sulfur was added. After reacting for one hr at 130°-140° C., morpholine was partially stripped out of the reaction mixture by blowing a slow stream of nitrogen through the mixture to raise the reaction temperature to 160° C. where it was held for two hr. The reaction product was isolated as an in Example II, and gave essentially the same yield and purity of 3 beta-hyroxy-25-homo-5-cholenic acid on hydrolysis. The ratio of steroid: sulfur: amine was 1:1.2:2.4.

EXAMPLE IV

This example demonstrates preparation of 3 beta-hydroxy-25-homo-5-cholenic acid from 25-homochol-5-en-3 beta-ol-24-one 3-acetate using aqueous amine polysulfides under pressure.

In a heavy walled glass tube with an inside diameter of 1 inch and 4 inches long, were charged 4.45 g of 25-homochol-5-en-3 beta-ol-24-one 3-acetate, 6 ml of a 25% aqueous solution of dimethylamine, 2.2 g of sulfur flowers and 10 ml of purified dioxane. The glass tube was then sealed and placed into a monel pressure vessel of 200 ml capacity and the pressure vessel was then filled three quarters full with the same reagents used in the glass tube, with the exception of the 24-keto compound. The pressure vessel was then heated in an oil bath for 7 hours to 150°-180° C. An internal pressure of 300 lb was developed at 180° C.

On opening, after cooling the charge to room temperature, there was a very slight positive pressure in the tube. The reaction mixture was a viscous product which gradually formed a flocculent solid on pouring into water. The resulting aqueous slurry was then acidified with hydrochloric acid and the reaction product filtered off and washed with water to obtain 5.0 g of a slightly pinkish powder. This reaction product was then hydrolyzed with ethanolic potassium hydroxide by refluxing for 12 hr at about 93° C. to covert the thioamide to the carboxylic acid. The product was recovered by dispersing in water and acidifying. On filtering and drying, a yield of 4.7 g was obtained, from which a substantial amount of 3 beta-hydroxy-25-homo-5-cholenic acid was isolated. After crystallization from ethylene dichloride, an acid having a melting point of 210°-212° C. was obtained. A mixture of this acid with an authentic sample of 3 beta-hydroxy-25-homo-5-cholenic acid showed no depression of the melting point. The ratio of steroid: sulfur: amine was 1:7:13.

EXAMPLE V

This example demonstrates preparation of 3 beta-hydroxy-25-homo-5-cholenic acid from 5-homochol-5-en-3 beta-ol-24-one 3-acetate using ammonium polysulfide and pyridine.

In a heavy glass tube with a 1" inside diameter and 4" long, a mixture of 1.5 g 25-homochol-5-en-3 beta-ol-24-one 3-acetate, 10 ml concentrated ammonia water, 7.5 g sulfur and 10 ml pyridine was sealed. The sealed tube was then placed into the 200 ml steel pressure vessel described in Example IV.

The steel pressure vessel was then heated in an oil bath for 6 hr to 150°-180° C. The vessel was then cooled to room temperature. There was a slight vacuum in the glass tube when it was opened. From the reaction mixture, there was isolated after hydrolysis with alcoholic potassium hydroxide, a small amount of a solid which gave in a t.l.c. analysis, the same $R_f$ as 3 beta-hydroxy-25-homo-5-cholenic acid. A 5% yield of 3 beta-hydroxy-25-homo-5-cholenic acid was obtained. The ratio of steroid: sulfur: amine (ammonia) was 1:65:78.

EXAMPLE VI

This example demonstrates preparation of 3 alpha, 6 alpha-dihydroxy-25-homocholanic acid from hyodesoxycholic acid.

(A) Preparation of 3 alpha, 6 alpha-hyodesoxycholic acid diacetate 3 alpha, 6 alpha-hyodesoxycholic acid diacetate was prepared by the procedure of June Bergstrom and Karin Paabo (Acta Chem. Scand. 9,699 (1955)) by reacting 1 m hyodesoxycholic acid with 12 m acetic anhydride in the presence of pyridine as a catalyst.

(B) Preparation of diacetoxy hyodesoxycholic acid chloride

Diacetoxy hyodesoxycholic acid chloride was prepared following the procedure in Example I (B) for 3 beta-acetoxy-5-cholenic acid chloride. 34 g of 3 alpha, 6 alpha-hyodesoxycholic acid diacetate prepared in (A) above was added slowly to 100 ml of thionylchloride and cooled to −15° C. Reaction temperature was held for 1 hr at −15° C. to −10° C., then allowed to warm up over the next 2 hr to 0° C. and then in one half hr to 30° C. Excess thionylchloride was distilled off under vacuum and collected in a receiver cooled to −15° C. The reaction flask was warmed in a water bath slowly from 30° C. to 60° C. The resinous mass which remained in the flask was dissolved in 100 ml of benzene and the solution was heated under vacuum up to 60° C. to remove benzene and residual thionylchloride. The yield was 35.4 g of diacetoxy hyodesoxycholic acid chloride.

The acid chloride could be obtained in crystalline form by dissolving in hexane and seeding with crystals that had formed in the top part of the reaction flask after distilling off benzene. The thin layer chromatogram of the crystalline form was the same as that of the resinous mass, so resinous product was used directly without crystallization in the next reaction step to produce 25-homocholan-3 alpha, 6 alpha-diol-24-one diacetate.

(C) Preparation of 25-homocholan-3 alpha, 6 alpha-diol-24-one diacetate

Diacetoxy hyodesoxycholic acid chloride from (B) was reacted with dimethyl cadmium using the following procedure:

A solution of dimethyl cadmium was prepared by reacting 0.17 m of methyl magnesium bromide in a mixture of 100 ml ether and 100 ml of dry benzene with 0.085 m of cadmium bromide at 20° C. 35.4 g of 3, 6-diacetoxyhyodesoxycholic acid chloride from (B) was dissolved in 150 ml dry benzene and added to the dimethyl cadmium. During addition, a gummy material precipitated and 200 ml of benzene was added to the solution over a period of 25 min. After reacting for 2 hr at 20° C., the reaction mixture was cooled to 15° C. and 50 g of ice was added and then added dropwise a solution of 23 ml concentrated hydrochloric acid diluted with 23 ml water. The two layers were separated and the benzene-ether layer evaporated in vacuo. The resinous residue weighed 34 g.

Crystals of 25-homocholan-3 alpha, 6 alpha-diol-24-one diacetate could be obtained either by recrystallization from hexane or acetone and water on prolonged standing. Melting point of the long needle crystals obtained from acetone was 154°-156° C. Analysis gave the following results:

| Found | Calc. for $C_{29}H_{46}O_5$ |
|---|---|
| %C: 73.15 | 73.38 |
| %H: 10.00 | 9.74 |

(D) Preparation of 3 alpha, 6 alpha-diacetoxy-25-homocholanic acid thiomorpholide The Willgerodt reaction was carried out by dissolving 4.8 g of the crude 25-homocholan-3 alpha, 6 alpha-diol-24-one diacetate from (C) above in 2 ml morpholine, then adding 0.51 g of sulfur and heating at reflux at 130°-135° C. for three hr. The crude reaction mixture was isolated by diluting the reaction mixture with morpholine and ethyl alcohol and then pouring the mixture slowly into water where it disperses readily. After about 1 hr agitation at room temperature, the reaction mixture was acidified and filtered to obtain 6.1 g of light tan colored powder which was 3 alpha, 6 alpha-diacetoxy-25-homocholanic acid thiomorpholide. The ratio of steroid: sulfur: amine was 1:1.6:4.5.

(E) Preparation of 25-homo-3 alpha, 6 alpha-hyodesoxycholanic acid 3.0 g of 3 alpha, 6 alpha-diacetoxy-25-homocholanic acid thiomorpholide from (D) was hydrolyzed for 5 hr in a solution of 8.5 g potassium hydroxide in 27 ml ethyl alcohol.

To isolate the 25-homo-3 alpha, 6 alpha-hyodesoxycholic acid, the above reaction mixture was evaporated under vacuum and residual alcohol and water were removed by refluxing with dichloroethane followed by evaporation. The residue was pulverized and then extracted with dichloroethane to remove nonacidic by-products. The insoluble fraction containing the potassium salt of the homohyodesoxycholanic acid was dispersed in water and acidified. 25-homo-3 alpha, 6 alpha-hyodesoxycholic acid could not be induced to crystallize but a light tan powder obtained by evaporating an acetone solution gave a carbon and hydrogen analyses which were in good agreement with the expected theoretical values. Analysis gave the following results:

| Found | Calc. for $C_{25}H_{42}O_4$ |
|---|---|
| %C: 73.44 | 73.83 |
| %H: 9.97 | 10.41 |

EXAMPLE VII

This example demonstrates process modifications of and further examples in the synthesis of homocholenic acid from cholenic acid.

(A) Preparation of 25-homochol-5-en-3 beta-ol-24-one 3-acetate

A 5 l, 3-necked round bottom flask equipped with a mechanical stirrer, constant pressure dropping funnel and nitrogen inlet was flame dried under a steady stream of nitrogen. Reaction was then performed under static nitrogen pressure. The reaction flask was charged with 1000 ml dry diethyl ether and 291 ml methyl magnesium bromide (2.94 g, 0.855 mole). To the stirred solution was added cadmium bromide (139 g, 0.512 mole) in four equal aliquots at five minute intervals. A mobile second layer separated under the diethyl ether layer soon after the third bromide addition. The dark grey reaction mixture was stirred at about 20° C. for 1 hr after the fourth bromide addition. Then 3 beta-acetoxycholenyl chloride (183.5 g, 0.407 mole), prepared by the procedure given in Example I (B) and dissolved in 680 ml benzene, was added to the mixture over about 20 min. As the chloride addition was continued, the lower layer of the reaction mixture became progressively more viscous until a thick, gummy mass was obtained. Reaction is essentially instantaneous and the reaction mixture should be worked up within 20 min after completion of the steroid chloride addition in order to minimize side reactions using the following procedure.

The ether layer was decanted off of the gummy reaction product in the reaction flask and the gum dissolved in 1000 ml ethylene dichloride. The flask was then cooled externally on ice and ice water was added slowly to the reaction mixture in the flask. After a short induction period, a heavy gel formed and occupied about 3 times the initial solution volume. Reaction of the gel with water was very exothermic. Addition of more water (about 1400 ml) caused the gel to become fluid again and produced a two phase solution containing a large amount of white precipitated salts. The mixture was acidified with 100 ml concentrated hydrochloric acid/water (1:1) to obtain a clear two phase solution consisting of a yellow upper organic layer and a pale yellow lower aqueous layer. The organic layer was separated, washed with water and concentrated to dryness under reduced pressure.

(B) Preparation of 25-homo-5-cholenic acid via 3 beta-acetoxy-25-homocholenic acid thiomorpholide using the procedure described above in Examples I (E) and I (G).

(C) Preparation of 25-homochol-5-en-3 beta-ol-24-one Method A. Hydrolysis of 25-homochol-5-en-3 beta-ol-24-one 3-acetate.

20 g of 25-homochol-5-en-3 beta-ol-24-one 3-acetate was hydrolyzed by standard procedures using potassium hydroxide (6 g) in methanol/water (300 ml: 10 ml) at reflux for 90 min. Recrystallization of the pale yellow solid from 90% aqueous acetone gave a product melting at 133°–134° C.

Method B. Reaction of 3 beta-hydroxy-5-cholenic acid with methyl lithium

A 1 1 3-necked round bottom flask was equipped with a condenser, mechanical stirrer and constant pressure dropping funnel. The apparatus was flamed under a stream of nitrogen and maintained under static nitrogen pressure. Dry tetrahydrofuran (250 ml distilled from Vitride) was introduced into the flask. A slurry of 3 beta-hydroxycholenic acid (13.1 g, 0.035 mole) was prepared by adding the solid steroid to the tetrahydrofuran. The flask was cooled externally on ice and methyl lithium (63 ml of a 1.84 m solution in ether, 0.115 mole) in 100 ml dry tetrahydrofuran was added to the rapidly agitated slurry dropwise over 90 min. After completion of the reaction, as determined by thin layer chromatography, the reaction mixture was poured slowly into dilute hydrochloric acid (30 ml concentrated hydrochloric acid in 1200 ml water) to obtain a white precipitate which was collected by filtration. Unreacted starting material was removed by dissolving the precipitate in 300 ml ethylene dichloride and treating the solution with 50 ml 10% sodium hydroxide for 1 hr. The organic layer was then separated and washed with water. Concentration and recrystallization of the white solid gave a product identical to that obtained in Method A.

(D) Preparation of 3 beta-hydroxy-25-homo-5-cholenic acid via 3 beta-hydroxy-25-homo-5-cholenic acid thiomorpholide Four grams (0.0108 mole) of 25-homochol-5-en-3 beta-ol-24-one was dissolved in 3.65 ml (0.0418 mole) hot morpholine under a static nitrogen atmosphere. The solution was refluxed and 0.61 g (0.0189 mole) elemental sulfur was added in one batch. The mixture immediately turned black. After refluxing 2 hr, the solution was diluted with 6 ml morpholine and the viscous solution was poured slowly into 125 ml water to obtain a granular tan precipitate. The precipitate was slurried and the slurry acidified with dilute hydrochloric acid. The tan solid was collected by suction filtration, dissolved in 100 ml carbon tetrachloride and separated from entrapped water. The organic layer was dried over anhydrous sodium sulfate, treated with 200 mg activated charcoal and refluxed for 1 hr. The charcoal was removed by filtration and the mother liquid concentrated to dryness to obtain a brown residue. The brown solid residue was dissolved in 26 ml ethanol and 1 ml water. Then 8 g potassium hydroxide was added and the mixture refluxed for four hr.

The solvent was removed under reduced pressure and the resulting light brown solid was broken up and extracted 3 times with boiling benzene (90 ml total). The solid was collected by suction filtration and washed with benzene and then hexane. Homocholenic acid was regenerated from the potassium salt by adding the solid to a rapidly stirred mixture of chloroform (40 ml), tetrahydrofuran (40 ml), water (40 ml) and concentrated hydrochloric acid (20 ml). After stirring for 2 hr the organic layer was separated and concentrated to dryness affording a fluffy, pale yellow solid. Recrystallization from ethylene dichloride gave 25-homo-5-cholenic acid identical to an authentic sample. The ratio of steroid: sulfur: amine was 1:1.8:4.0.

While the invention has been described with reference to certain specific embodiments thereof, it is understood that it is not to be so limited since alterations and changes may be made therein which are within the full and intended scope of the appended claims.

What is claimed is:

1. A process of preparing a steroidal acid of the formula

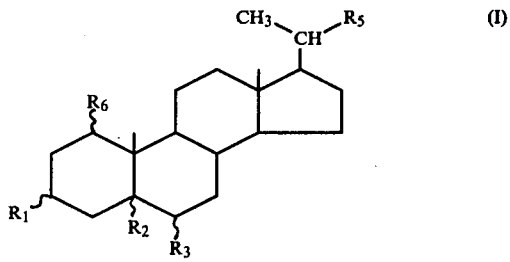

which comprises reacting a steroidal ketone of the formula

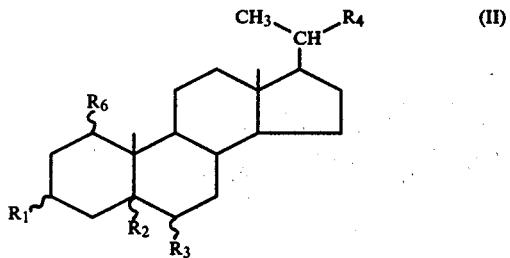

wherein:
$R_1$ is hydrogen; hydroxy; lower alkyloxy; tetrahydropyranyloxy; aryloxy; alkyl; alkanoyloxy or aroyloxy;
$R_2$ is hydrogen; hydroxy; lower alkyloxy; tetrahydropyranyloxy; aryloxy; alkyl; alkanoyloxy or aroyloxy;
$R_3$ is hydrogen; hydroxy; lower alkyloxy; tetrahydropyranyloxy; aryloxy; alkyl; alkanoyloxy or aroyloxy; with the proviso that $R_1$ and $R_2$ together or $R_2$ and $R_3$ together may form a carbon-carbon bond;
$R_4$ is $-(CH_2)_nCO(CH_2)_mCH_3$;
$R_5$ is $-(CH_2)_{n+m+1}COOH$;
$R_6$ is hydrogen; hydroxy; lower alkyloxy; tetrahydropyranyloxy; aryloxy; alkyl; alkanoyloxy or aroyloxy; and
n is 0 to 4, m is 0 to 4 and sum of n+m is 0 to 4 in formulas (I) and (II) above
with from about 1 m to about 70 m of sulfur and about 1 m to about 80 m of a base selected from the group consisting of ammonia, primary amines and secondary amines to obtain a thioamide and thereafter hydrolyzing the thioamide to obtain the steroidal acid.

2. The process of claim 1 wherein the steroidal ketone is selected from the group consisting of 25-homochol-5-en-3beta-ol-24-one and esters thereof, 25-homocholan-3alpha, 6alpha-diol-24-one and esters thereof, 24-norchol-5-en-3beta-ol-22-one and esters thereof and homochol-5-en-3beta-ol-22-one and esters thereof.

3. The process of claim 1 wherein the steroidal ketone is 25-homochol-5-en-3beta-ol-24-one and esters thereof.

4. The process of claim 1 wherein the steroidal ketone is 25-homocholan-3alpha, 6alpha-diol-24-one and esters thereof.

5. The process of claim 1 wherein the steroidal ketone is 24-norchol-5-en-3beta-ol-22-one and esters thereof.

6. The process of claim 1 wherein the steroidal ketone is 25-homochol-5-en-3beta-ol-22-one and esters thereof.

7. The process of claim 1 wherein the reaction between ketone, sulfur and base is at a temperature of about 125° to about 180° C.

8. The process of claim 2 wherein the reaction between ketone, sulfur and base is at a temperature of about 125° to about 180° C.

9. The process of claim 3 wherein the reaction between ketone, sulfur and base is at a temperature of about 125° to about 180° C.

10. The process of claim 4 wherein the reaction between ketone, sulfur and base is at a temperature of about 125° to about 180° C.

11. The process of claim 1 wherein the base is morpholine.

12. The process of claim 1 wherein the base is ammonia.

13. The process of claim 1 wherein the thioamide is hydrolyzed by refluxing in alcoholic potassium hydroxide.

14. 3 beta-acetoxy-25-homo-5-cholenic acid-25-thiomorpholide.

15. 3 beta-hydroxy-25-homo-5-cholenic acid-25-morpholide.

16. 3 alpha, 6 alpha-dihydroxy-25-homocholanic acid-25-thiomorpholide.

17. 3 alpha, 6 alpha-dihydroxy-25-homocholanic acid-25-thiomorpholide diacetate.

18. 1 alpha, 3 beta-dihydroxy-25-homocholanic acid-25-thiomorpholide.

* * * * *